United States Patent
Liu et al.

(10) Patent No.: US 11,760,810 B2
(45) Date of Patent: Sep. 19, 2023

(54) MODIFIED IMMUNOGLOBULIN HINGE REGIONS TO REDUCE HEMAGGLUTINATION

(71) Applicant: The Board of Trustees of the Leland Stanford Junior University, Stanford, CA (US)

(72) Inventors: Jie Liu, Palo Alto, CA (US); Irving L. Weissman, Stanford, CA (US); Ravindra Majeti, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 338 days.

(21) Appl. No.: 17/223,778

(22) Filed: Apr. 6, 2021

(65) Prior Publication Data
US 2021/0253740 A1    Aug. 19, 2021

Related U.S. Application Data (62) Division of application No. 16/340,537, filed as application No. PCT/US2017/058569 on Oct. 26, 2017, now Pat. No. 10,995,152.

(60) Provisional application No. 62/413,018, filed on Oct. 26, 2016.

(51) Int. Cl.
| | |
|---|---|
| C07K 16/46 | (2006.01) |
| C07K 14/705 | (2006.01) |
| C07K 16/28 | (2006.01) |
| A61K 38/00 | (2006.01) |

(52) U.S. Cl.
CPC ............ *C07K 16/46* (2013.01); *C07K 14/705* (2013.01); *C07K 16/2803* (2013.01); *A61K 38/00* (2013.01); *C07K 16/2896* (2013.01); *C07K 2317/24* (2013.01); *C07K 2317/53* (2013.01)

(58) Field of Classification Search
None
See application file for complete search history.

(56) References Cited

U.S. PATENT DOCUMENTS

| | | | |
|---|---|---|---|
| 10,995,152 B2 * | 5/2021 | Liu | C07K 16/28 |
| 2004/0175824 A1 | 9/2004 | Sun et al. | |
| 2006/0204496 A1 | 9/2006 | Kojima | |
| 2011/0077383 A1 | 3/2011 | Dall'Acqua et al. | |
| 2011/0263830 A1 | 10/2011 | Goetsch et al. | |
| 2013/0011394 A1 | 1/2013 | Knoetgen | |
| 2013/0323236 A1 | 12/2013 | Humphreys et al. | |
| 2014/0271582 A1 | 9/2014 | Forman et al. | |
| 2015/0017169 A1 | 1/2015 | Humphreys et al. | |
| 2015/0018529 A1 | 1/2015 | Humphreys et al. | |
| 2015/0183874 A1 | 7/2015 | Liu et al. | |
| 2015/0239958 A1 | 8/2015 | Wurch | |
| 2017/0166645 A1 | 6/2017 | Weissman et al. | |

FOREIGN PATENT DOCUMENTS

| | | |
|---|---|---|
| CN | 104327 | 2/2015 |
| WO | WO2008/085878 | 7/2008 |
| WO | WO2009091547 | 7/2009 |
| WO | WO2009091601 | 7/2009 |
| WO | WO2011034969 | 3/2011 |
| WO | WO2011/066501 | 6/2011 |
| WO | WO2011143624 | 11/2011 |
| WO | WO2011143624 A2 | 11/2011 |
| WO | WO2012/075184 | 6/2012 |
| WO | WO20121151468 | 11/2012 |
| WO | WO2013109752 | 7/2013 |
| WO | WO20131109752 | 7/2013 |
| WO | WO20131181253 | 12/2013 |
| WO | WO2014/031687 | 3/2014 |
| WO | WO2014/055515 | 4/2014 |
| WO | WO2014094122 | 6/2014 |
| WO | WO20141102179 | 7/2014 |
| WO | WO2014123580 | 8/2014 |
| WO | WO2014124028 | 8/2014 |
| WO | WO2014149477 | 9/2014 |
| WO | WO2014179132 | 11/2014 |
| WO | WO2014186761 | 11/2014 |
| WO | WO2015/022420 | 2/2015 |
| WO | WO2015041987 | 3/2015 |
| WO | WO2015105995 | 7/2015 |
| WO | WO2016044021 | 3/2016 |
| WO | WO2016118754 | 7/2016 |
| WO | WO2016138306 | 9/2016 |
| WO | WO20161191305 | 12/2016 |
| WO | WO2017035480 | 3/2017 |
| WO | WO2017055582 | 4/2017 |
| WO | WO2017214096 A1 | 12/2017 |

OTHER PUBLICATIONS

Edwards et al. (2003) "The Remarkable Flexibility of the Human Antibody Repertoire; Isolation of Over One Thousand Different Antibodies to a Single Protein, BLyS" J Mol Bioi. 334(1): 103-118.

(Continued)

*Primary Examiner* — Phuong Huynh
(74) *Attorney, Agent, or Firm* — Pamela J. Sherwood; Bozicevic, Field & Francis LLP (57) ABSTRACT

Polypeptide compositions comprising a human immunoglobulin constant region with a modified IgG4 hinge region having an N-terminal deletion of 1, 2, 3, 4, 5 amino acids, relative to a native human IgG4 hinge sequence are provided. In some embodiments the hinge sequence further comprises the amino acid substitution S228P (Eu numbering). Polypeptides comprising the modified sequence optionally comprise a binding moiety specific for an epitope that is present on red blood cells; and can provide for reduced agglutination of hematopoietic cells compared to a comparable polypeptide with a native hinge region.

5 Claims, 5 Drawing Sheets
Specification includes a Sequence Listing.

(56) References Cited

OTHER PUBLICATIONS

Silva et al., (2015) "The S228P mutation prevents in vivo and in vitro IgG4 Fab-arm exchange as demonstrated using a f:ombination of novel quantitative immunoassays and physiological matrix preparation", J. Bioi. Chem., 290(9), American Society for Biochemistry and Molecular Biology, Rockville, MD. pp. 5462-5469.

Yang et al., (2015) "Comprehensive Analysis of the Therapeutic IgG4 Antibody Pembrolizumab: Hinge Modification Blocks Half Molecule Exchange In Vitro and In Vivo", J Parm Sci., vol. 104, Issue 12. Elsevier, New York City, NY.4002-4014, vol. 104, Issue 12, Elsevier, New York City, NY. pp. 4002-4014.

Glaser et al.,(2005) "Novel Antibody Hinge Regions for Efficient Production of CH2 Domain-deleted Antibodies", The journal of Biological Chemistry, vol. 280, No. 50, American Society for biochemistry and Molecular Biology, Rockville, MD, pp. 41494-41503.

Horgan et al. (1993) "Studies on antigen binding by intact and hinge-deleted chimeric antibodies", The Journal of Immunology. American Association of Immunologists. US. vol. • 150. No. 12, pp. 5400-5407.

Liu et al. (2015) "Pre-Clinical Development of a Humanized Anti-CD47 Antibody with Anti-Cancer Therapeutic Potential". Plos One. 1-23.

Lloyd et al.,(2009) Modelling the human immune response: performance of a 1011 human antibody repertoire against a broad panel of therapeutically relevant antigens"Protein Engineering, Design & Selection" 22:159-168.

Raitt et al. (1989) "in Immunology" second edition, Gower Medical Publishing New York, pp. 5.8 and 5.9.

\* cited by examiner

Sequence of reference hu-IgG4 constant region

| CH1 | 1-98 | SEQ ID NO:1 | ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRV |
| --- | --- | --- | --- |
| H | 99-110 | SEQ ID NO:2 | ESKYGPPCPSCP |
| CH2 | 111-220 | SEQ ID NO:3 | APEFLGGPSVFLFPPKPKDTLMISRTPEVTCVVVDVSQEDPE VQFNWYVDGVEVHNAKTKPREEQFNSTYRVVSVLTVLHQDWL NGKEYKCKVSNKGLPSSIEKTISKAK |
| CH3 | 221-327 | SEQ ID NO:4 | GQPREPQVYTLPPSQEEMTKNQVSLTCLVKGFYPSDIAVEWE SNGQPENNYKTTPPVLDSDGSFFLYSRLTVDKSRWQEGNVFS CSVMHEALHNHYTQKSLSLSLGK |

Sequence of modified hu-IgG4 constant region

| CH1 | 1-98 | SEQ ID NO:1 | ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRV |
| --- | --- | --- | --- |
| H | 99-110 | SEQ ID NO:5 | PPCP S/P CP |
| CH2 | 111-220 | SEQ ID NO:3 | APEFLGGPSVFLFPPKPKDTLMISRTPEVTCVVVDVSQEDPE VQFNWYVDGVEVHNAKTKPREEQFNSTYRVVSVLTVLHQDWL NGKEYKCKVSNKGLPSSIEKTISKAK |
| CH3 | 221-327 | SEQ ID NO:4 | GQPREPQVYTLPPSQEEMTKNQVSLTCLVKGFYPSDIAVEWE SNGQPENNYKTTPPVLDSDGSFFLYSRLTVDKSRWQEGNVFS CSVMHEALHNHYTQKSLSLSLGK |

5F9 VH and modified G4H construct (VH and modified hinge underlined)

(SEQ ID NO:6)

QVQLVQSGAEVKKPGASVKVSCKASGYTFTNYNMHWVRQAPGQRLEWMGTIYPGNDDTSYNQKF
KDRVTITADTSASTAYMELSSLRSEDTAVYYCARGGYRAMDYWGQGTLVTVSSASTKGPSVFPL
APCSRSTSESTAALGCLVKDYFPEPVTVSSGLYSLSSVVTVPSSS
LGTKTYTCNVDHKPSNTKVDKRVPPCPPPCPAPEFLGGPSVFLFPPKPKDTLMISRTPEVTCVVV
DVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYK
TTPPVLDSDGSFFLYSRLTVDKSRWQEGNVFSCSVMHEALHNHYTQKSLSLSLGK

FIG. 5B

5F9 VL and modified G4H construct (SEQ ID NO:7)

DVVMTQSPLSLPVTPGEPASISCRSSQSIVYSNGNTYLGWYLQKPGQSPKLLIYKVSNRFSGVPD
RFSGSGSGTDFTLKISRVEAEDVGVYHCFQGSHVPYTFGGGTKVEIKASTKGPSVFPLAPCSRST
SESTAALGCLVKDYFPEPVTVSSGLYSLSSVVTVPSSSLGTKTYT
CNVDHKPSNTKVDKRVPPCPPPCPAPEFLGGPSVFLFPPKPKDTLMISRTPEVTCVVVDSQEDP
EVQFNWYVDGVEVHNAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK

SEQUENCE LISTING

```
<160> NUMBER OF SEQ ID NOS: 8

<210> SEQ ID NO 1
<211> LENGTH: 98
<212> TYPE: PRT
<213> ORGANISM: Homo sapiens

<400> SEQUENCE: 1

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val
```

<210> SEQ ID NO 2
<211> LENGTH: 12
<212> TYPE: PRT
<213> ORGANISM: Homo sapiens

<400> SEQUENCE: 2

```
Glu Ser Lys Tyr Gly Pro Pro Cys Pro Ser Cys Pro
 1               5                  10
```

<210> SEQ ID NO 3
<211> LENGTH: 110
<212> TYPE: PRT
<213> ORGANISM: Homo sapiens

<400> SEQUENCE: 3

```
Ala Pro Glu Phe Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110
```

<210> SEQ ID NO 4
<211> LENGTH: 107
<212> TYPE: PRT
<213> ORGANISM: Homo sapiens

<400> SEQUENCE: 4

```
Gly Gln Pro Arg Glu Pro Gln Val Tyr Thr Leu Pro Pro Ser Gln Glu
 1               5                  10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
```

<210> SEQ ID NO 5
<211> LENGTH: 7
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (5)..(5)
<223> OTHER INFORMATION: X is S or P

<400> SEQUENCE: 5

Pro Pro Cys Pro Xaa Cys Pro
1               5

<210> SEQ ID NO 6
<211> LENGTH: 439
<212> TYPE: PRT
<213> ORGANISM: Artificial Sequence
<220> FEATURE:
<223> OTHER INFORMATION: Synthetic Sequence

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
            275                 280                 285

Asn Ser Thr Tyr Arg Val Val Ser Val Leu Thr Val Leu His Gln Asp
            290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
            325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
            405                 410                 415

Cys Ser Val Met His Glu Ala Leu His Asn His Tyr Thr Gln Lys Ser
            420                 425                 430

Leu Ser Leu Ser Leu Gly Lys
            435

<210> SEQ ID NO 7
<211> LENGTH: 434
<212> TYPE: PRT
<213> ORGANISM: Artificial Sequence
<220> FEATURE:
<223> OTHER INFORMATION: Synthetic Sequence

<400> SEQUENCE: 7

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Phe Gln Gly
            85                  90                  95

Ser His Val Pro Tyr Thr Phe Gly Gly Gly Thr Lys Val Glu Ile Lys
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Ser Leu Gly Thr Lys Thr
            180                 185                 190

```
Tyr Thr Cys Asn Val Asp His Lys Pro Ser Asn Thr Lys Val Asp Lys
        195                 200                 205
Arg Val Pro Pro Cys Pro Pro Cys Pro Ala Pro Glu Phe Leu Gly Gly
        210                 215                 220
Pro Ser Val Phe Leu Phe Pro Pro Lys Pro Lys Asp Thr Leu Met Ile
225                 230                 235                 240
Ser Arg Thr Pro Glu Val Thr Cys Val Val Asp Val Ser Gln Glu
        245                 250                 255
Asp Pro Glu Val Gln Phe Asn Trp Tyr Val Asp Gly Val Glu Val His
        260                 265                 270
Asn Ala Lys Thr Lys Pro Arg Glu Glu Gln Phe Asn Ser Thr Tyr Arg
        275                 280                 285
Val Val Ser Val Leu Thr Val Leu His Gln Asp Trp Leu Asn Gly Lys
        290                 295                 300
Glu Tyr Lys Cys Lys Val Ser Asn Lys Gly Leu Pro Ser Ser Ile Glu
305                 310                 315                 320
Lys Thr Ile Ser Lys Ala Lys Gly Gln Pro Arg Glu Pro Gln Val Tyr
                325                 330                 335
Thr Leu Pro Pro Ser Gln Glu Glu Met Thr Lys Asn Gln Val Ser Leu
            340                 345                 350
Thr Cys Leu Val Lys Gly Phe Tyr Pro Ser Asp Ile Ala Val Glu Trp
            355                 360                 365
Glu Ser Asn Gly Gln Pro Glu Asn Asn Tyr Lys Thr Thr Pro Pro Val
            370                 375                 380
Leu Asp Ser Asp Gly Ser Phe Phe Leu Tyr Ser Arg Leu Thr Val Asp
385                 390                 395                 400
Lys Ser Arg Trp Gln Glu Gly Asn Val Phe Ser Cys Ser Val Met His
                405                 410                 415
Glu Ala Leu His Asn His Tyr Thr Gln Lys Ser Leu Ser Leu Ser Leu
            420                 425                 430
Gly Lys

<210> SEQ ID NO 8
<211> LENGTH: 12
<212> TYPE: PRT
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (10)..(10)
<223> OTHER INFORMATION: X is S or P

<400> SEQUENCE: 8

Glu Ser Lys Tyr Gly Pro Pro Cys Pro Xaa Cys Pro
1               5                   10
```

MODIFIED IMMUNOGLOBULIN HINGE REGIONS TO REDUCE HEMAGGLUTINATION

CROSS-REFERENCE TO RELATED APPLICATIONS

This application claims the benefit and is a Divisional of application Ser. No. 16/340,537, filed Apr. 9, 2019, now U.S. Pat. No. 10,995,152, which is a 371 application and claims the benefit of PCT Application No. PCT/US2017/058569, filed Oct. 26, 2017, which claims benefit of U.S. Provisional Patent Application No. 62/413,018, filed Oct. 26, 2016, which applications are incorporated herein by reference in their entirety.

BACKGROUND OF THE INVENTION

The development of therapeutic mAbs has substantially impacted treatment of some types of cancer. Conventionally these recombinant proteins specifically bind cancer cells and either block signaling pathways or mark them for destruction by the immune system. However, targeted mAbs exist for only a few cancers, even the most effective mAbs may require combination therapy with conventional chemotherapy, and often produce an incomplete therapeutic response. In many patients, the disease becomes resistant to mAb treatment by loss of the antibody target (when the molecule is not essential for tumor cell survival) or by developing resistance to tumor killing. Usually patients experience a relapse of their disease.

CD47 has been identified as a key molecule mediating cancer cell evasion of phagocytosis by the innate immune system. CD47 appears to be an indispensable means by which cancer cells, including cancer stem cells, overcome intrinsic expression of their prophagocytic, "eat me," signals. The progression from normal cell to cancer cell involves changes in genes and/or gene expression that trigger programmed cell death (PCD) and programmed cell removal (PCR). Many of the steps in cancer progression subvert the multiple mechanisms of PCD, and the expression of the dominant antiphagocytic signal, CD47, may represent an important checkpoint.

CD47 expression is increased on the surface of cancer cells from a large number of diverse human tumor types including the following primary malignancies: head and neck, melanoma, breast, lung, ovarian, pancreatic, colon, bladder, prostate, leiomyosarcoma, glioblastoma, medulloblastoma, oligodendroglioma, glioma, lymphoma, leukemia, and multiple myeloma. In murine xenograft studies, it has been shown that CD47-blocking antibodies inhibit human cancer growth and metastasis by enabling the phagocytosis and elimination of cancer stem cells and cancer cells from various hematologic malignancies and several solid tumors.

However, erythrocytes also express CD47 on the cell surface. The loss or blockade of CD47 on the cell surface coupled with gain of prophagocytic signals leads to phagocytic clearance of erythrocytes. An initial transient anemia can be caused by administration of the anti-CD47 antibody by clearing aged erythrocytes and inducing reticulocytosis. The blood population of red blood cells then shifts to younger cells that express CD47 but do not have prophagocytic signals. In addition to the extended effect of anemia and compensation, there can be an acute effect of hemagglutination immediately after administration of an anti-CD47 antibody. To reduce acute hemagglutination it is therefore desirable to provide an antibody in a manner that reduces undesirable hemagglutination.

The present invention provides antibodies having reduced hemagglutination in humans.

PUBLICATIONS

United States Patent Application 20150239958, relates to a process for the modulation of the antagonistic activity of a monoclonal antibody". United States Patent Applications 20150018529, 20130323236 and 20150017169 relate to bispecific modified IgG4 antibodies. United States Patent Application 20120238729 relates to modified antibody constant regions. United States Patent Application 20110077383 relates to hinge domain engineering.

Modifications of the human IgG4 hinge region to block half molecule exchange, specifically the S228P (Kabat numbering) substitution have been described in the art, e.g. Yang et al. (2015) J. Pharm. Sci. doi: 10.1002/jps.24620; Silva et al. (2015) J. Biol. Chem. 290(9):5462-9.

Publications relating to the use of anti-CD47 agents are described, for example, in published international application serial nos. US2009/000319; US2009/000224; US2010/048992; US2011/036535; US2013/021937; US2014/038485; US2014/014905; US2014/018743; US2014/035167; US2014/055680; US2016/019633; US2015/010650; US2015/049150; US2016/014334; US2016/049016; and in U.S. provisional application Ser. Nos. 62/380,177 and 62/301,981; each of which is herein specifically incorporated by reference.

SUMMARY OF THE INVENTION

Polypeptide compositions, including antibody compositions, and methods of use thereof are provided. The polypeptides of the invention comprise a human immunoglobulin constant region with a modified IgG4 hinge region having an N-terminal deletion of 1, 2, 3, 4, 5 amino acids, relative to a native human IgG4 hinge sequence. In some embodiments the hinge sequence further comprises the amino acid substitution S228P (Kabat numbering). The modified hinge sequence may be referred to herein as a "modified G4H". Polypeptides comprising a modified G4H, herein referred to as "modified G4H polypeptides" optionally comprise a binding moiety specific for an epitope that is present on hematopoietic cells; and can provide for reduced agglutination of hematopoietic cells, e.g. hemagglutination, compared to a comparable polypeptide with a native hinge region.

The epitope present on hematopoietic cells include, without limitation, a CD47 protein, e.g. human CD47. The specific binding moiety may be, without limitation, a VL sequence that binds specifically to CD47, a VH sequence that binds specifically to CD47, a VH-VL sequence that binds specifically to CD47, a soluble SIRPα sequence that binds specifically to CD47, an affinity matured soluble SIRPα sequence that binds specifically to CD47, and the like. Suitable binding moieties include, without limitation, the variable region of Hu5F9, CC-9002; TTI-621 and bivalent, tetravalent, etc. high affinity SIRPα polypeptides.

In some embodiments of the invention, the modified G4H is directly fused to one or more immunoglobulin constant region domains. The constant region domain sequences may be any of the known constant region sequences, including without limitation human IgA, IgD, IgE, IgG, IgM constant region domains. In some embodiments the constant region domain sequence is a human IgG sequence, e.g. IgG1, IgG2, IgG3, IgG4, etc. In some embodiments it is a human IgG4 sequence. The modified G4H may be directly fused to one or both of CH2 and CH1 domains, for example where the CH1 sequence is fused to the amino terminus and the CH2 sequence is fused to the carboxy terminus of the hinge. The modified G4H may be directly fused to a CH3 domain, e.g. in generating a minibody.

In some embodiments the modified G4H is incorporated into an intact heavy chain, e.g. replacing the native hinge region in a polypeptide chain comprising a VH region fused to a CH1-H-CH2-CH3 constant region. In some embodiments the heavy chain thus formed is paired with a suitable light chain. In some embodiments the heavy and light chain form a dimeric or tetrameric protein, where the binding moiety formed by the VH and VL domains may provide a binding moiety specific for an epitope present on red blood cells. An antibody may also be provided as a bi-specific or multispecific antibody reactive with a second antigen, particularly including cancer antigens.

In some embodiments, the modified G4H is directly fused to a CH2 or CH3 region at its carboxy terminus, and is directly fused to a binding moiety on the amino terminus. Such a modified G4H polypeptide may further comprise an antibody CH3 constant domain joined to the CH2 domain, for example in a configuration of B-H-CH2-CH3, where B designates the specific binding domain. The binding moiety may be specific for an epitope present on hematopoietic cells, including without limitation CD47. The binding moiety may include, without limitation, a soluble SIRPα sequence that specifically binds to CD47.

Embodiments include isolated polypeptides comprising a modified G4H and derivatives and fragments thereof, including labeled derivatives; pharmaceutical formulations comprising one or more of the modified G4H comprising polypeptides; and cell lines that produce these polypeptides. Modified G4H comprising polypeptides may be labeled with a detectable label, immobilized on a solid phase and/or conjugated with a heterologous compound. Also provided are amino acid sequences of the polypeptides. Where the modified G4H polypeptide is an antibody, the antibody may be human, humanized, or chimeric, where the constant region sequences, i.e. the CH1, CH2, CH3 sequences, are of human origin, including without limitation IgG4 sequences.

The modified G4H polypeptides described herein can be used for any therapeutic purpose suitable for the binding moiety of the polypeptide. In some embodiments, where the binding moiety is specific for CD47, the compositions are used in therapeutic modalities as known in the art concerning blockade or activation of CD47. In some embodiments, methods are provided for enhancing phagocytosis of CD47 expressing cells by blockade of the interaction between CD47 expressed on a cell targeted for phagocytosis, and SIRPα expressed on a phagocytic cell. Such methods may comprise contacting a targeted cell with an effective dose of modified G4H polypeptide comprising a CD47 binding moiety. The targeted cells may be, without limitation, cancer cells, virus-infected cells, etc. Treatment may be systemic or localized, e.g. delivery by intratumoral injection, etc.

The invention further provides: isolated nucleic acid encoding the modified G4H polypeptides and variants thereof; a vector comprising that nucleic acid, optionally operably linked to control sequences recognized by a host cell transformed with the vector; a host cell comprising that vector; a process for producing the polypeptide comprising culturing the host cell so that the nucleic acid is expressed and, optionally, recovering the antibody from the host cell culture (e.g. from the host cell culture medium). The invention also provides a composition comprising one or more of the modified G4H polypeptides and a pharmaceutically acceptable carrier or diluent. This composition for therapeutic use is sterile and may be lyophilized, e.g. being provided as a pre-pack in a unit dose with diluent and delivery device, e.g. inhaler, syringe, etc.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
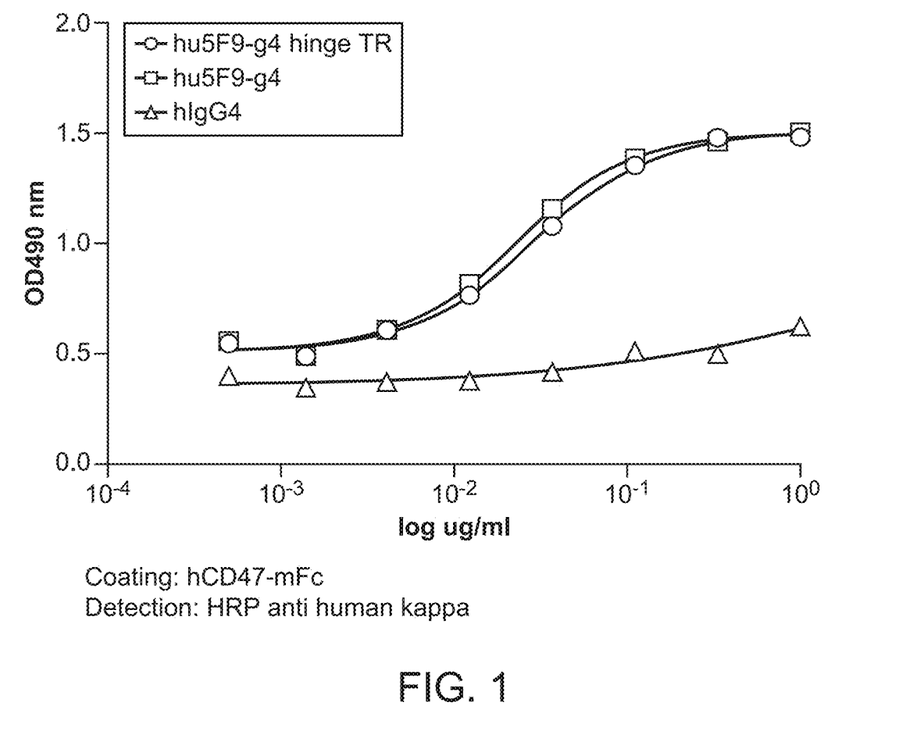
FIG. 1. Binding of anti-CD47 Ab Hu5F9-G4 with modified/truncated hinge region (TR) to CD47 not reduced compared to parental Hu5F9-G4 Ab with non-modified hinge region. CD47 binding assay was done by coating a 96-well plate with 1 μg/ml huCD47/mFc fusion protein in phosphate-buffered saline (PBS) for 16 hr at 4° C. After blocking for 1 hr with 0.4% BSA in PBS at room temperature, 10 μg/ml of Hu5F9-G4 or Hu5F9-G4 with truncated hinge was added and in 1/3 sequential dilutions, and incubated for 1 hr at room temperature. Plates were subsequently washed three times and incubated with HRP-conjugated goat anti-human kappa-specific antibody for 1 hr at room temperature. After washing, plates were developed with OPT. The reaction was stopped with 2N $H_2SO_4$, and OD was measured at 490 nM.
Figure 2:
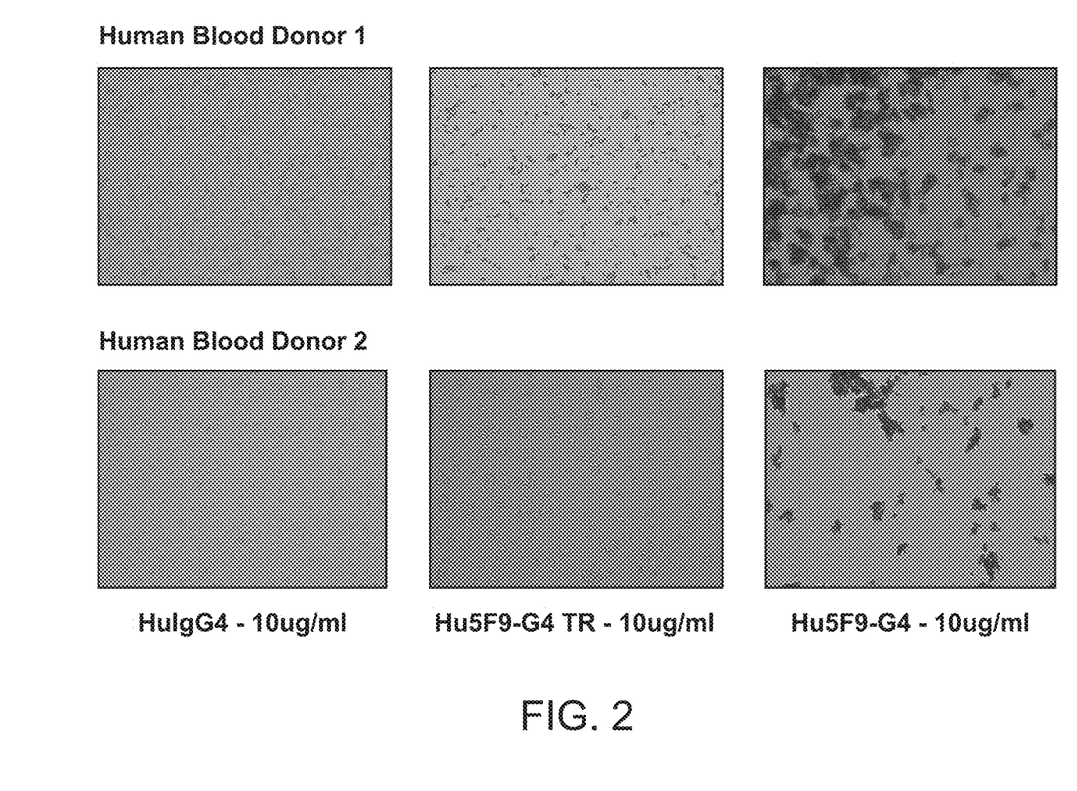
FIG. 2. Modification/truncation of hinge region (TR) reduces agglutination of human red blood cells by CD47-binding antibody Hu5F9-G4 compared to Hu5F9-G4 with non-modified hinge region. Human blood was obtained from two healthy donors. Incubate 100 ul of the blood with 10 ug/ml of antibodies as indicated above at 37° C. for 2 hr. Blood smear was done using 5 ul of the blood/antibody mixture and stained with Giemsa. RBC agglutination was examined under the microscope.
Figure 3:
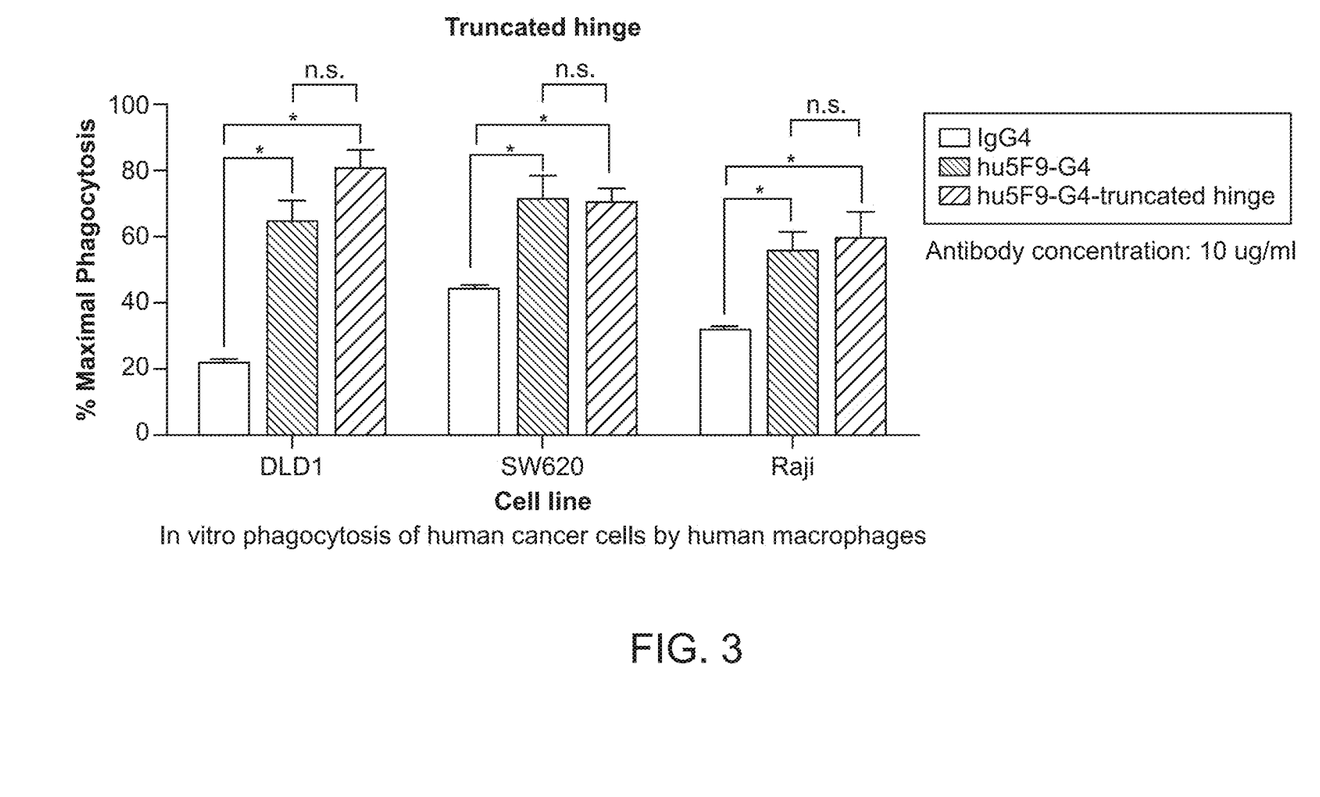
FIG. 3. Modification/truncation of hinge region (TR) does not affect therapeutic efficacy of CD47-binding antibody Hu5F9-G4 compared to Hu5F9-G4 with non-modified hinge region. DLD1, SW620, and Raji cells were Calcein-labeled and incubated with human peripheral blood-derived macrophages in the presence of 10 ug/ml of Hu5F9-G4, Hu5F9-G4 with truncated hinge or an isotype control antibody for 2 hr at 37° C. Macrophages were then labelled with AlexaFluor 647 anti-human CD206. Cells were washed and analyzed using flow cytometry. The percentage of phagocytosis was calculated as the percentage of FITC+target cells within AlexaFluor 647+macrophages.
Figure 4:
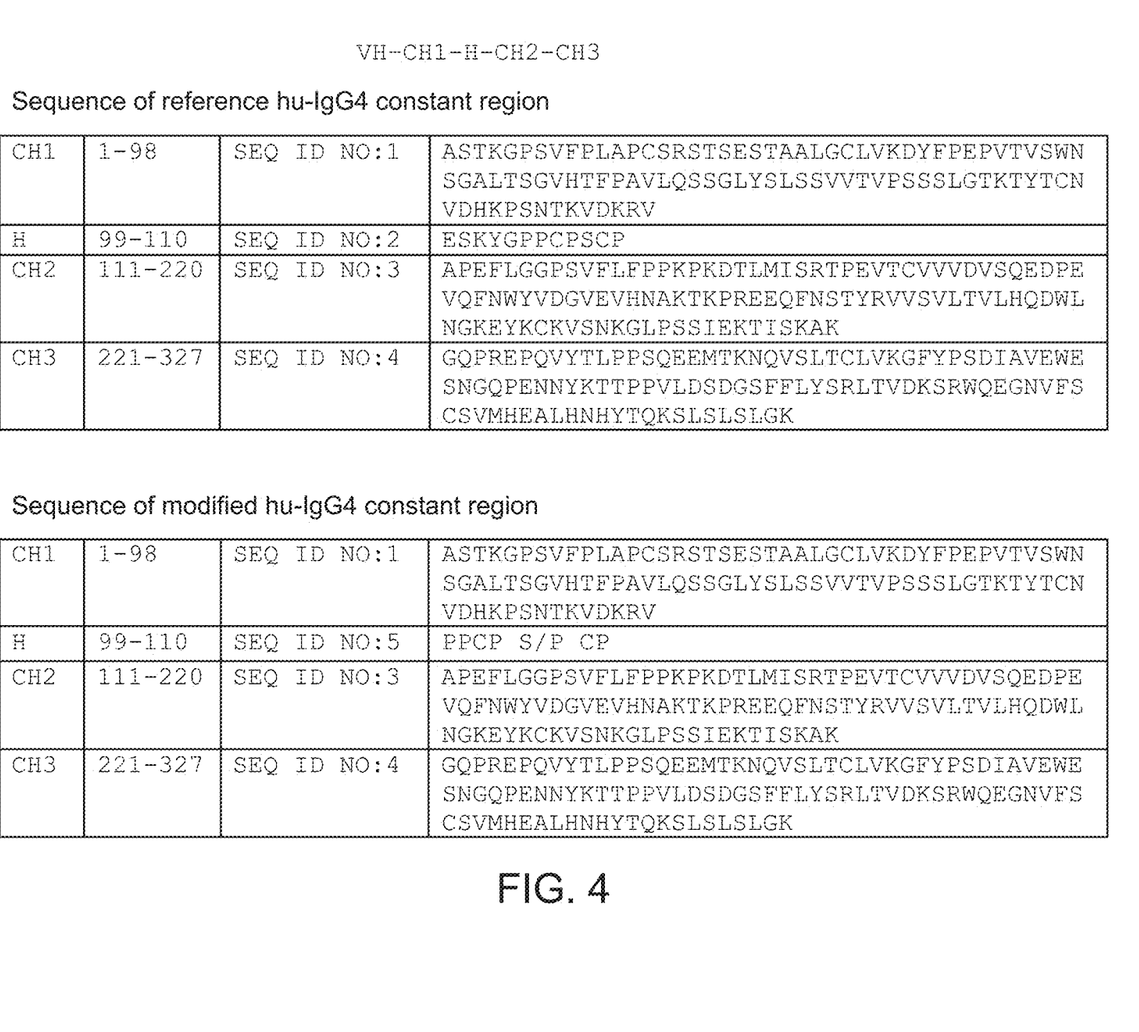
FIG. 4. Sequences of the native human IgG4 constant regions, and sequence of the modified G4 hinge sequence.
Figure 5A:
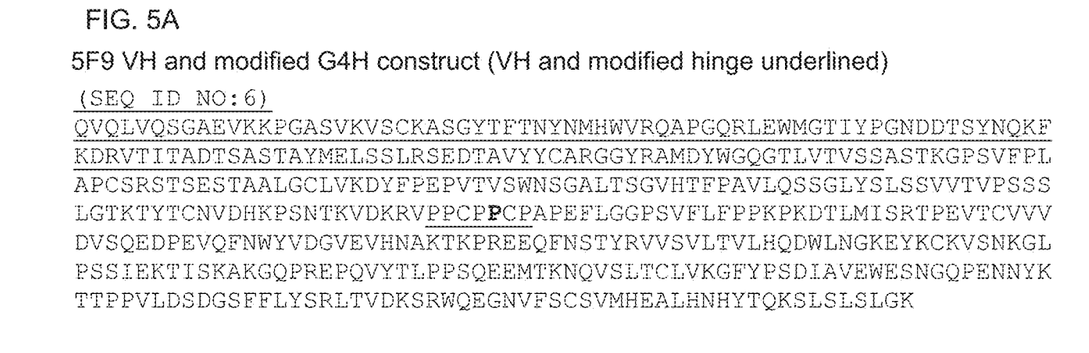
FIG. 5A-5B. Sequences of 5F9 variable region constructs.
Figure 5B:
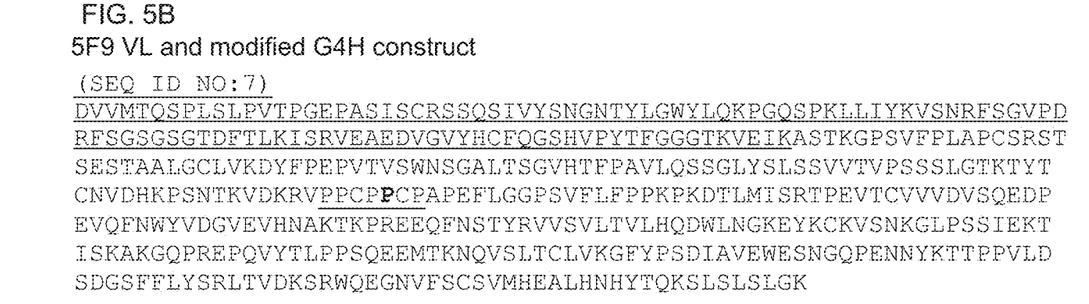

The present invention relates to polypeptides comprising a modified IgG4 hinge sequence, which can provide for an unexpected reduction in hemagglutination, e.g. when the antibody binds to a protein present on red blood cells. The modified hinge can be utilized in the context of an intact antibody, or fragments thereof, e.g. Fc region sequences for fusion to a binding moiety of interest. Also disclosed are nucleic acid, and amino acid sequence of such polypeptides.

"Native antibodies and immunoglobulins" are typically heterotetrameric glycoproteins of about 150,000 daltons, composed of two light (L) chains and two heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains, in the configuration $V_H$-$C_{H1}$-H-$C_{H2}$-$C_{H3}$. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (see, for example, Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Immunoglobulin G (IgG) is one of the most abundant proteins in human serum, accounting for about 10-20% of plasma protein. It is the major class of the five classes of immunoglobulins in human beings, IgM, IgD, IgG, IgA, and IgE. IgG can be further divided in four subclasses, named, in order of decreasing abundance IgG1, IgG2, IgG3, and IgG4. Although they are more than 90% identical on the amino acid level, each subclass has a unique profile with respect to antigen binding, immune complex formation, complement activation, triggering of effector cells, half-life, and placental transport.

Similar to the other isotypes, the IgG 50 kDa γ heavy (H) chain consists of an N-terminal variable domain (VH) and three constant domains (CH1, CH2, CH3), with an additional "hinge region" between CH1 and CH2. The residues most proximal to the hinge region in the CH2 domain of the Fc part are responsible for effector functions of antibodies as it contains a largely overlapping binding site for C1q (complement) and IgG-Fc receptors (FcγR) on effector cells of the innate immune system. A highly conserved N-linked glycosylation site at position 297 is located at the interface between the two CH2/CH3. The interface between the CH2-CH3 domains also contains the binding site for the neonatal Fc receptor (FcRn), responsible for the prolonged half-life of IgG, placental passage, and transport of IgG to and from mucosal surfaces.

The hinge region forms a flexible linker between the Fab arms and the Fc region. Length and flexibility of the hinge region varies extensively among the IgG subclasses. For the purposes of the present invention, the hinge is defined as the "genetic hinge", i.e. the sequence encoded by hinge exons. The N-terminus of the CH2 domain may be referred to as the "genetic CH2, lower hinge".

The native hinge sequence of IgG1 encompasses 15 amino acids and is very flexible. IgG2 has a shorter hinge than IgG1, with 12 amino acid residues, and the hinges of IgG2 are more rigid due to a poly-proline helix, stabilized by inter-heavy chain disulfide bridges. The native hinge region of IgG4 also contains 12 amino acids and is thus shorter than that of IgG1. Its flexibility is intermediate between that of IgG1 and IgG2.

The native IgG4 hinge sequence is as follows: (SEQ ID NO:2) ESKYGPPCPSCP. Two isomers of IgG4 differing in the disulfide bonding of hinge cysteines coexist. The core hinge of IgG is formed by a CXXC motif, also found in redox-reactive proteins such as thioredoxins. Compared to IgG1, with a relatively rigid CPPC motif, intra-chain disulfide bonds are more easily formed between these cysteines found at positions 226 and 229 in IgG4, which possesses a CPSC core hinge. The result is an observable amount of non-covalently linked half-molecules (consisting of one heavy and one light chain, HL, as opposed to the classical configuration of $H_2L_2$) in addition to covalently linked inter-chain isomers. An S228P mutant of IgG4, thus with an IgG1-core hinge, does not form half-molecules, which is in agreement with the finding that this species does not occur in IgG1. The process is reversible but depends on redox conditions. Formation of the intra-chain isomer (half-molecules) is an important step in the "Fab arm exchange." Thus, the hinge of G4 may be defined as:

E S K Y G P P C P S/P C P　　　　　　(SEQ ID NO:8)

The modified hinge provided herein has a deletion of 1, 2, 3, 4, or 5 amino acids at the amino terminus of the G4 hinge (SEQ ID NO:8). In some embodiments the modified hinge has a sequence:

P P C P S/P C P　　　　　　(SEQ ID NO:5)

The deleted amino acids correspond to residues 226, 227, 228, 229, and 230 of IGHG4 (Kabat numbering).

The modified G4H is usually directly fused to a CH2 constant region domain at the carboxy terminus, including without limitation a human IgG1, IgG2, IgG3, IgG4 CH2 domain. By direct fusion it is meant that the amino terminal proline of the modified G4H forms a bond with the amino terminal residue of the CH2 domain. The modified G4H can also be fused to CH3, for example, to make a minibody. Alternatively a CH2 domain may be directly fused to a CH3 domain, as in a native Fc configuration. The CH3 domain may be from the same source as the CH2 domain, or may be heterologous. In some embodiments the CH2 and CH3 domains are a human IgG sequence.

"Specific binding moiety", as used herein, refers to an agent, usually a polypeptide, that interacts specifically to associate with a binding partner of interest where the relative binding constant (Kd) is sufficiently strong to allow, for example, detection of binding to the protein by a detection means; physiologically relevant association, etc. In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-19}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Suitable specific binding members include agents that specifically bind CD47 and/or SIRPα (i.e., anti-CD47 agents), or that otherwise block the interaction between CD47 and SIRPα.

"Binding affinity" generally refers to the strength of the sum total of noncovalent interactions between a single binding site of a molecule (e.g., an antibody or other binding molecule) and its binding partner (e.g., an antigen or receptor). The affinity of a molecule X for its partner Y can generally be represented by the dissociation constant (Kd). Affinity can be measured by common methods known in the art, including those described herein. Low-affinity antibodies bind antigen (or receptor) weakly and tend to dissociate readily, whereas high-affinity antibodies bind antigen (or receptor) more tightly and remain bound longer.

Specific binding moieties of interest include an immunoglobulin variable region domain. A native variable region comprises a dimer of one heavy chain and one light chain variable domain in tight, non-covalent association. However a binding moiety in a polypeptide of the invention may comprise a VH in the absence of a VL sequence, or a VL in the absence of a VH. Even a single variable domain (i.e. half of an Fv comprising only three hypervariable regions specific for an antigen) has the ability to recognize and bind antigen, although the affinity may be lower than that of two domain binding site.

As is known in the art, variable regions are comprised of framework and hypervariable sequences. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.).

Other specific binding moieties of interest include, for example, ligand/receptor, or receptor and counter-receptor binding partners, where the binding moiety may be a native binding partner, an affinity matured binding partner, etc.

In some embodiments, the binding moiety specifically binds to an epitope present on red blood cells. As used in this invention, the term "epitope" means any antigenic determinant on an antigen to which the paratope of an antibody, or a specific binding moiety, binds. Epitopic determinants usually consist of chemically active surface groupings of molecules such as amino acids or sugar side chains and usually have specific three dimensional structural characteristics, as well as specific charge characteristics.

In some embodiments, the epitope present on red blood cells is an epitope of CD47. CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2007) J.B.C. 282:14567-75; and the role of SIRPα cis dimerization in CD47 binding is discussed by Lee et al. (2010) J.B.C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo. CD47 is also expressed on red blood cells, particularly aged red blood cells; on tumor cells, on virus-infected cells, etc.

Certain binding moieties specific for CD47, and modified-G4H polypeptides comprising such binding moieties may be referred to herein as an "anti-CD47 agent", which refers to an agent that binds to CD47 and in doing so reduces the binding of CD47 to SIRPα. Non-limiting examples of suitable anti-CD47 reagents include SIRPα reagents, including without limitation high affinity SIRPα polypeptides and anti-CD47 antibodies or antibody fragments. Such an agent may up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, or at least 200%) compared to phagocytosis in the absence of the agent. In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1, 2004). Thus, in some embodiments, the anti-CD47 agent does not directly induce cell death of a CD47-expressing cell.

A modified-G4H anti-CD47 agent, upon contact with red blood cells, will result in reduced agglutination relative to a comparable agent comprising a native hinge sequence, e.g. reducing hemagglutination. The reduction in hemagglutination may be at least about 10%, at least about 20%, at least about 30%, at least 40%, at least about 50%, or more.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference). Clone CC-9002 is disclosed in WO2013119714, herein specifically incorporated by reference. Suitable anti-CD47 antibodies include fully human, humanized or chimeric versions of such antibodies. Humanized antibodies (e.g., hu5F9) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

In certain embodiments, an anti-CD47 antibody comprises a heavy chain sequence as set forth in SEQ ID NO:6 or SEQ ID NO:7, which may be combined with a suitable light chain sequence.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα. A SIRPα reagent is a fusion protein, e.g., directly fused to a modified G4H sequence provided herein. By direct fusion, it is meant that the amino terminal residue of the modified-G4H peptide is joined to the carboxy terminus of the SIRPα sequence, e.g. in the absence of a linker. The modified-G4H may be directly fused to a CH2 sequence of an immunoglobulin, as described herein, to provide part or whole of an immunoglobulin Fc region. An example of a SIRPa agent is TTI-621, disclosed for use in clinical trial NCT02663518, which may be altered to utilize a modified-G4H sequence.

In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. A SIRPα reagent is a fusion protein, e.g., directly fused to a modified G4H sequence provided herein. By direct fusion, it is meant that the amino terminal residue of the modified-G4H peptide is joined to the carboxy terminus of the SIRPa sequence, e.g. in the absence of a linker. The modified-G4H may be directly fused to a CH2 sequence of an immunoglobulin, as described herein, to provide part or whole of an immunoglobulin Fc region.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, or may be made by recombinant DNA methods.

The monoclonal antibodies herein include hybrid and recombinant antibodies produced by splicing a variable (including hypervariable) domain of an anti-CD47 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to an anti-CD47 antibody fused to an "epitope tag". The epitope tag polypeptide has enough residues to provide an epitope against which an antibody can be made, yet is short enough such that it does not interfere with activity of the CD47 antibody. The epitope tag preferably is sufficiently unique so that the antibody specific for the epitope does not substantially cross-react with other epitopes. Suitable tag polypeptides generally have at least 6 amino acid residues and usually between about 8-50 amino acid residues (preferably between about 9-30 residues). Examples include the c-myc tag and the 8F9, 3C7, 6E10, G4, B7 and 9E10 antibodies thereto (Evan et al., Mol. Cell. Biol. 5(12):3610-3616 (1985)); and the Herpes Simplex virus glycoprotein D (gD) tag and its antibody (Paborsky et al., Protein Engineering 3(6):547-553 (1990)).

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.)

As used herein, a "target cell" is a cell expressing CD47 on the surface, where masking or otherwise altering the CD47 positive phenotype (e.g., by administration of an anti-CD47 agent) results in increased phagocytosis. Usually a target cell is a mammalian cell, for example a human cell.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

A "therapeutically effective dose" or "therapeutic dose" is an amount sufficient to effect desired clinical results (i.e., achieve therapeutic efficacy). A therapeutically effective dose can be administered in one or more administrations. For purposes of this invention, a therapeutically effective dose of an anti-CD47 agent is an amount that is sufficient to palliate, ameliorate, stabilize, reverse, prevent, slow or delay the progression of the disease state (e.g., cancer) by increasing phagocytosis of a target cell (e.g., a target cell). Thus, a therapeutically effective dose of an anti-CD47 agent reduces the binding of CD47 on an target cell, to SIRPα on a phagocytic cell, at an effective dose for increasing the phagocytosis of the target cell.

A therapeutically effective dose of an anti-CD47 agent can depend on the specific agent used, but is usually about 5 mg/kg body weight or more (e.g., about 8 mg/kg or more, about 10 mg/kg or more, about 15 mg/kg or more, about 20 mg/kg or more, about 25 mg/kg or more, about 30 mg/kg or more, about 35 mg/kg or more, or about 40 mg/kg or more), or from about 10 mg/kg to about 40 mg/kg (e.g., from about 10 mg/kg to about 35 mg/kg, or from about 10 mg/kg to about 30 mg/kg). The dose required to achieve and/or maintain a particular serum level is proportional to the amount of time between doses and inversely proportional to the number of doses administered. Thus, as the frequency of dosing increases, the required dose decreases. The optimization of dosing strategies will be readily understood and practiced by one of ordinary skill in the art.

In some embodiments, a priming dose is defined a dose (i.e., an amount) that is sufficient to cause compensatory reticulocytosis, without undue anemia, and is administered prior to a therapeutically effective dose. In some embodiments a priming dose is defined as a dose that causes an anemia that is not worsened by subsequent doses.

The specific appropriate priming dose of an anti-CD47 agent can vary depending on the nature of the agent used and on numerous subject-specific factors (e.g., age, weight, etc.). Examples of suitable priming doses of an anti-CD47 agent include from about 0.5 mg/kg to about 5 mg/kg, from about 0.5 mg/kg to about 4 mg/kg, from about 0.5 mg/kg to about 3 mg/kg, from about 1 mg/kg to about 5 mg/kg, from about 1 mg/kg to about 4 mg/kg, from about 1 mg/kg to about 3 mg/kg, about 1 mg/kg, about 2 mg/kg, about 3 mg/kg, about 4 mg/kg, about 5 mg/kg.

A "maintenance dose" is a dose intended to be a therapeutically effective dose. For example, in experiments to determine the therapeutically effective dose, multiple different maintenance doses may be administered to different subjects. As such, some of the maintenance doses may be therapeutically effective doses and others may be subtherapeutic doses.

A "loading dose" may be used to achieve a therapeutic level of antibody before switching to a maintenance dose. A loading dose can be the same be the same or higher or lower than the maintenance dose, but will generally provide for a higher overall delivery of the agent over a given period of time. For example, a loading dose can be the same or lower than a maintenance dose, but delivered more frequently, e.g. daily, every other day, every third day, twice weekly, weekly, and the like. Alternatively a loading dose can be a higher dose than a maintenance dose, and delivered at the same periodicity, or more frequently, e.g. daily, every other day, every third day, twice weekly, weekly, and the like.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells.

The term "sample" with respect to a patient encompasses blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations, such as cancer cells. The definition also includes samples that have been enriched for particular types of molecules, e.g., nucleic acids, polypeptides, etc.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample"

includes a sample comprising target cells or normal control cells or suspected of comprising such cells or biological fluids derived therefrom (e.g., cancerous cell, infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell from a patient can also include non-inflicted cells.

Compositions

In one aspect, the present invention is directed to polypeptides, including without limitation antibodies and specific binding moieties fused to an antibody Fc sequence, which comprise a modified-G4H sequence as described above. In addition to intact antibodies, and Fc constructions, the polypeptides can also include, for example, single heavy chains and fragments thereof, provided that a modified-G4H sequence is included.

The invention also provides isolated nucleic acids encoding the modified-G4H polypeptides, vectors and host cells comprising the nucleic acid, and recombinant techniques for the production of the polypeptides. Nucleic acids of interest may be at least about 80% identical to the provided nucleic acid sequences, at least about 85%, at least about 90%, at least about 95%, at least about 99%, or identical.

For recombinant production of the polypeptide, the nucleic acid encoding it is inserted into a replicable vector for further cloning (amplification of the DNA) or for expression. DNA encoding the polypeptide is readily isolated and sequenced using conventional procedures (e.g., by using oligonucleotide probes that are capable of binding specifically to genes encoding the heavy chain constant regions). Many vectors are available. The vector components generally include, but are not limited to, one or more of the following: a signal sequence, an origin of replication, one or more marker genes, an enhancer element, a promoter, and a transcription termination sequence.

The polypeptides may be produced recombinantly not only directly, but also as a fusion polypeptide with a heterologous or homologous polypeptide, which include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

Suitable host cells for cloning or expressing the DNA are the prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2). Host cells are transformed with the above-described expression or cloning vectors for polypeptide production and cultured in conventional nutrient media modified as appropriate for inducing promoters, selecting transformants, or amplifying the genes encoding the desired sequences.

The polypeptide composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma1$, $\gamma2$, or $\gamma4$ heavy chains (Lindmark et al., J. Immunol. Meth. 62:1-13 (1983)). Protein G is recommended for human $\gamma3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the polypeptide of interest and contaminants may be subjected to low pH hydrophobic interaction chromatography using an elution buffer at a pH between about 2.5-4.5, preferably performed at low salt concentrations (e.g., from about 0-0.25M salt).

Methods of Use

The modified-G4H polypeptides can be used for any purpose suitable for the specific binding moiety. Where the binding moiety is specific for CD47, e.g. a SIRP polypeptide, and anti-CD47 variable region, the composition may find use in the modulation of phagocytosis, including the methods set forth in International Application US2009/000319, herein specifically incorporated by reference in its entirety. Of interest are embodiments where decreased hemagglutination is desired. For example, the polypeptide compositions may be administered in vivo to increase phagocytosis of cancer cells expressing CD47.

In some embodiments of the invention, an effective priming dose of an anti-CD47 agent is provided. An initial dose of a CD47 binding agent, including but not limited to a priming dose, may also lead to hemagglutination for a period of time immediately following infusion. Without being bound by the theory, it is believed that the initial dose of a multivalent CD47 binding agent may cause cross-linking of RBC bound to the agent. The use of the modified G4H reduces hemagglutination.

The modified-G4H polypeptides can be used in vitro and in vivo as therapeutic agents, to monitor the course of disease therapy, etc. Thus, for example, by measuring the increase or decrease in the number of cells expressing CD47, particularly cancer cells expressing CD47, it can be determined whether a particular therapeutic regimen aimed at ameliorating disease is effective.

The polypeptides of the invention may be used in vitro in immunoassays in which they can be utilized in liquid phase or bound to a solid phase carrier. In addition, the polypeptides in these immunoassays can be detectably labeled in various ways. Examples of types of immunoassays which can utilize monoclonal antibodies of the invention are flow cytometry, e.g. FACS, MACS, immunohistochemistry, competitive and non-competitive immunoassays in either a direct or indirect format; and the like. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The modified G4H polypeptides can be bound to many different carriers and used in detection assays. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

Therapeutic formulations comprising one or more polypeptides of the invention are prepared for storage by mixing the polypeptide having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to accomplish the desired therapy.

A therapeutic dose may be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The polypeptide need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The polypeptide is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the polypeptide is suitably administered by pulse infusion, particularly with declining doses of the antibody.

For the prevention or treatment of disease, the appropriate dosage of polypeptide will depend on the type of disease to be treated, as defined above, the severity and course of the disease, whether the polypeptide is administered for preventive purposes, previous therapy, the patient's clinical history and response to the polypeptide, and the discretion of the attending physician. The polypeptide is suitably administered to the patient at one time or over a series of treatments.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the modified-G4H polypeptide. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Modification of the Hinge Region (Truncated Hinge) of CD47-Binding Agents to Mitigate Cellular Agglutination CD47-binding agents can cause agglutination of CD47-expressing cells, with agglutination of red blood cells being the most prominent example. Therapy with such CD47-binding agents, e.g. CD47-binding antibodies, can potentially cause significant side effects. Hu5F9-g4 can also cause acute death in AML-engrafted mice, possibly due to agglutination of AML cells. Preliminary data showed that hu5f9-g4 with truncated hinge reduced the acute death of mice having high burden of the disease.

Hematopoietic cell agglutination can limit the therapeutic use of such agents or require specific dosing strategies. Identified herein is a modification of the hinge region of CD47-binding agents that reduces the agglutination of CD47 expressing cells. The hinge region is a portion of the immunoglobulin heavy chain and connects the Fab with the Fc region. Thus the hinge region is part of monoclonal antibodies but can also be engineered to connect other molecules to Fc regions. Therefore, this invention applies to all antibody related molecules that contain a hinge region, including CD47 binding agents.

The humanized anti-CD47 antibody, Hu5F9-G4, was tested for its effects on pre-transfusion blood typing and cross-matching in preparation of strategies for management of patients who might need transfusion during Hu5F9-G4 treatment. Hu5F9-G4 was incubated with RBCs from non-human primates and human donors. Hu5F9-G4 did not induce in vitro hemolysis of human RBCs, even in the presence of complement-containing serum. The study showed no evidence of hemagglutination (HA) in seven NHP specimens. However, HA was observed in all 14 human donor blood samples in the presence of 10 micrograms/mL of Hu5F9-G4. Unlike most cases of agglutination-related autoimmune hemolytic anemia where HA is caused by cold IgM agglutinins, the agglutination caused by Hu5F9-G4, an IgG4, occurred at 37° C. but not at 4° C. While RBC agglutination can be seen in several conditions (usually in association with infectious agents, both with and without clinical sequelae), the clinical significance of the agglutination seen here is uncertain.

What is claimed is:

1. A polynucleotide sequence encoding an antibody that specifically binds to human CD47, comprising a heavy chain amino acid sequence of SEQ NO:6; and an immunoglobulin light chain variable region comprising residues 1-112 of SEQ ID NO:7.

2. A polynucleotide sequence encoding an antibody that specifically binds to human CD47, comprising a light chain amino acid sequence of SEQ NO:7; and an immunoglobulin heavy chain variable region comprising residues 1-117 of SEQ ID NO:6.

3. A polynucleotide vector comprising the polynucleotide sequence of claim 1 or claim 2.

4. The vector of claim 3, comprising one or more of a signal sequence, an origin of replication, one or more marker genes, an enhancer element, a promoter, and a transcription termination sequence operably linked to the polynucleotide sequence encoding an antibody.

5. A cell comprising the vector of claim 3.

* * * * *